(12) United States Patent
Lai et al.

(10) Patent No.: US 9,782,916 B2
(45) Date of Patent: Oct. 10, 2017

(54) WASTE PLASTIC CONTAINER RECYCLING SYSTEM AND METHOD THEREOF

(71) Applicant: ORIENTAL INSTITUTE OF TECHNOLOGY, New Taipei (TW)

(72) Inventors: Chin-Lun Lai, New Taipei (TW); Jun-Horng Chen, Taipei (TW)

(73) Assignee: Oriental Institute of Technology, New Taipei (TW)

( * ) Notice: Subject to any disclaimer, the term of this patent is extended or adjusted under 35 U.S.C. 154(b) by 0 days.

(21) Appl. No.: 15/232,240

(22) Filed: Aug. 9, 2016

(65) Prior Publication Data

US 2017/0043504 A1 Feb. 16, 2017

(30) Foreign Application Priority Data

Aug. 10, 2015 (TW) .............................. 104125931 A

(51) Int. Cl.
| | |
|---|---|
| *B07C 5/342* | (2006.01) |
| *B29B 17/02* | (2006.01) |
| *G01N 21/31* | (2006.01) |
| *G01N 33/00* | (2006.01) |
| *G01J 3/00* | (2006.01) |
| *B29L 31/00* | (2006.01) |

(52) U.S. Cl.
CPC ............ *B29B 17/02* (2013.01); *B07C 5/3422* (2013.01); *G01J 3/00* (2013.01); *G01N 21/31* (2013.01); *G01N 33/00* (2013.01); *B07C 2501/0054* (2013.01); *B29B 2017/0203* (2013.01); *B29B 2017/0279* (2013.01); *B29L 2031/712* (2013.01); *G01N 2033/0081* (2013.01)

(58) Field of Classification Search
CPC . B29B 17/02; B29B 2017/0213; B07C 5/342; B07C 5/3422; B29L 2031/712; B29L 2031/7158; G01N 21/31; G01N 33/00
See application file for complete search history.

(56) References Cited

U.S. PATENT DOCUMENTS 6,313,423 B1 * 11/2001 Sommer ................. B07C 5/342
209/577

\* cited by examiner

*Primary Examiner* — Mark Beauchaine
(74) *Attorney, Agent, or Firm* — Muncy, Geissler, Olds & Lowe, P.C.

(57) ABSTRACT

A waste plastic container recycling system and a method thereof are provided for determining whether the spectrum of a waste container to be recycled belongs to any one of spectrums of plastic materials and for classifying waste containers of different plastic materials since the plastic materials have the different spectral characteristics. Accordingly, the waste plastic container recycling system and the method thereof can accurately recognize the waste containers of different plastic materials regardless of the appearance, or damage, deformation or concealment of the label on the waste containers.

6 Claims, 4 Drawing Sheets

WASTE PLASTIC CONTAINER RECYCLING SYSTEM AND METHOD THEREOF

BACKGROUND OF THE INVENTION

Field of the Invention

The present invention relates to a recycling system and method thereof, and more particularly to a waste plastic container recycling system and method thereof.

Description of the Prior Art

A common waste container automatic recycling system is mostly composed of following structures and operated according to following operation principles. A body of a waste container recycling system has singular or plural container input(s) for different categories. When a user puts a container to be recycled therein, a plurality of sensors inside the body detects a weight, volume, transparency, electric conductivity/magnetic conductivity, appearance or other categorization labels (for example, a barcode, sensible label) and determines a type of the container to be recycled.

Nowadays, the waste container recycling system usually determines plastic types based on density and transparency. However, the waste container recycling system does not have a mechanism which can precisely distinguish waste plastic containers made of similar physical/chemical characteristics (for example, PET, PP, PE, PVC and other plastic materials). In addition, if there is liquid residue in the waste plastic containers, a possibility of error identification elevates.

Therefore, if the waste container recycling system can automatically exclude the liquid residue in the waste plastic container and can precisely distinguish the waste plastic containers made of different plastic materials, the waste plastic containers can be precisely categorized.

The present invention has arisen to mitigate and/or obviate the afore-described disadvantages.

SUMMARY OF THE INVENTION

The major object of the present invention is to provide a waste plastic container recycling system for determining if a waste container is made of one of a plurality of plastic materials so as to recycle the waste container accordingly. The waste plastic container recycling system includes a light generator, a sensing probe, an optical spectrum analyzer and a controller. The light generator is arranged in a vicinity of the waste container for emitting a light to the waste container. The sensing probe is arranged in the vicinity of the waste container. The sensing probe is for receiving a light signal which is produced from the light entering the waste container or from the light being reflected by the waste container. The optical spectrum analyzer is electrically connected to the sensing probe for receiving the light signal and produces a spectrum of the waste container based on the light signal. The controller is electrically connected to the optical spectrum analyzer. The controller has a specific spectrum of respective ones of the plastic materials saved therein, determining if the spectrum of the waste container is identical to any one of the specific spectrums. If the controller determines the spectrum of the waste container is identical to any one of the specific spectrums, a process of recycling the waste container is conducted.

The major object of the present invention is to provide a method for recycling a waste plastic container, which is adapted for a waste plastic container recycling system to determine if a waste container is made of one of a plurality of plastic materials so as to recycle the waste container accordingly. The method for recycling a waste plastic container includes following steps of: projecting light to the waste container; receiving a light signal which is produced from the light entering the waste container or from the light being reflected by the waste container; receiving the light signal and producing a spectrum of the waste container based on the light signal; saving specific spectrums of respective ones of the plastic materials in the waste plastic container recycling system, determining if the spectrum of the waste container is identical to any one of specific spectrums, wherein if the spectrum of the waste container is identical to any one of the specific spectrums, a process of recycling the waste container is conducted.

Given the above, the waste plastic container recycling system and the method thereof are provided to recognize the plastic material that the waste plastic container is made of through the optical spectrum analyzing technology, and to exclude the liquid residue in the waste plastic container beforehand. Therefore, the waste plastic container recycling system and the method thereof of the present invention can precisely determine a plurality of waste plastic containers which have similar physical/chemical characteristics so as to categorize the waste plastic containers precisely and accurately.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

A waste plastic container recycling system and a method thereof are provided, the plastic materials which have similar physical/chemical characteristics have different spectrum characteristics, the waste plastic container recycling system can determine if a spectrum of a waste container to be recycled is one of the spectrums of the plastic materials so that the waste containers made of different plastic materials can be precisely categorized. In addition, the waste container tilts toward a ground and is arranged around an extension portion of an operation member of the waste plastic container recycling system, and a liquid residue in the waste container can be excluded so that the waste plastic container recycling system can obtain the spectrum of the waste container in higher precision to categorize the waste containers precisely and accurately.

Figure 1:
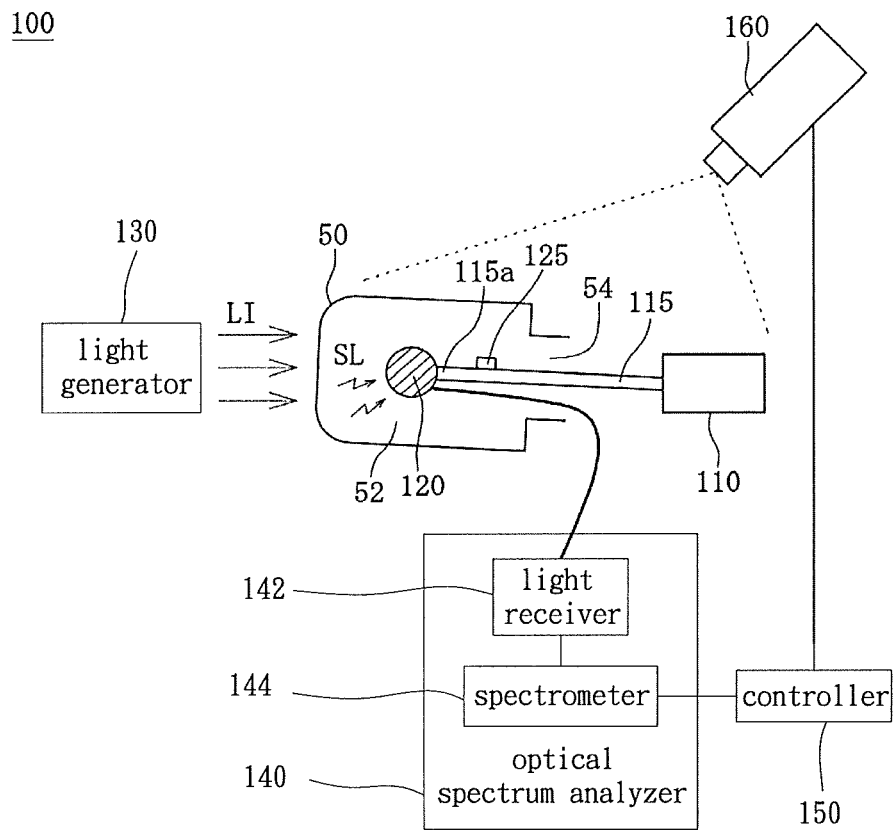
FIG. 1 is a drawing showing an embodiment of a waste plastic container recycling system of the present invention.

Please refer to FIG. 1 for an embodiment of a waste plastic container recycling system of the present invention. The waste plastic container recycling system 100 is for determining if a waste container 50 is made of one of a plurality of plastic materials so as to recycle the waste container 50 based on the plastic material thereof. In this embodiment, the plurality of plastic materials are numbered from 1 to 7 respectively: PET, HDPE, PVC, LDPE, PP, PS and other materials. The plastic materials may be at least one of the plastic materials in number 1 to 7, but not limited thereto.

The waste plastic container recycling system 100 includes an operation member 110, a sensing probe 120, a light generator 130, an optical spectrum analyzer 140 and a controller 150. The operation member 110 is arranged in a part of an interior of the waste plastic container recycling system 100 and has an extension portion 115. The extension portion 115 is inserted in a receiving space 52 of the waste container 50. Specifically, the waste container 50 has an opening 54, the opening 54 communicates with the receiving space 52, and an acute angle is included between the opening 54 and a ground. That is, when the waste container 50 is arranged around the extension portion 115, the opening 54 of the waste container 50 tilts toward the ground in an angle so that a liquid residue in the receiving space 52 can be excluded through the opening 54 without influencing a determination of the plastic material of the waste container 50. The operation member 110 is fixedly arranged in the part in the interior of the waste plastic container recycling system 100 so that the waste container 50 can be fixedly positioned to prevent the determination of the plastic material of the waste container 50 from being influenced.

In addition, the extension portion 115 of the operation member 110 may be provided with a cleaning nozzle 125 for cleaning an interior surface of the waste container 50. Specifically, the cleaning nozzle 125 is connected to an air-jetting (water-jetting) device (not shown). Therefore, when the waste container 50 is arranged around the extension portion 115, the cleaning nozzle 125 cleans the interior surface of the waste container 50 so as to elevate accuracy when determining if the waste container 50 is made of plastic materials. In this embodiment, the cleaning nozzle 125 is disposed around the extension portion 115 so as to clean the interior surface of the waste container 50 evenly. The cleaning nozzle 125 may be arranged on other parts of the extension portion 115, but not limited thereto.

The light generator 130 is arranged in a vicinity of the waste container 50 for emitting a light LI to the waste container 50. The sensing probe 120 is arranged in the vicinity around and outside of the waste container 50 and corresponds to the light generator 130 to receive a light signal SL which is produced by the light LI entering the waste container 50. That is, the light generator 130 emits the light LI, and the light LI enters the waste container 50 to configuration the light signal SL which represents a reflective light. The sensing probe 120 receives the light signal SL and transmits the light signal SL to the optical spectrum analyzer 140 to produce a spectrum in a wavelength range needed. In this embodiment, the sensing probe 120 is connected to the extension portion 115 and preferably on a top portion 115a of the extension portion 115 so as to receive the light signal SL more preferably. The sensing probe 120 may be arranged in other parts of the receiving space 52 of the waste container 50 where can receive the light signal SL, but not limited thereto.

The optical spectrum analyzer 140 is electrically connected to the sensing probe 120 for receiving the light signal SL and produces a spectrum of the waste container 50 based on the light signal SL. Specifically, the optical spectrum analyzer 140 includes a light receiver 142 and a spectrometer 144. The light receiver 142 collects the light signal SL received by the sensing probe 120 and measure relative data of the light signal SL, such as luminous flux and color. The spectrometer 144 receives the relative data of the light signal SL through a gating thereof and to produce the spectrum of the waste container 50 bases on the relative data of the light signal SL. In this embodiment, the light receiver 142 is an integrating sphere. The light receiver 142 may be other devices which can measure the relative data of the light signal SL, but not limited thereto.

Figure 2A:
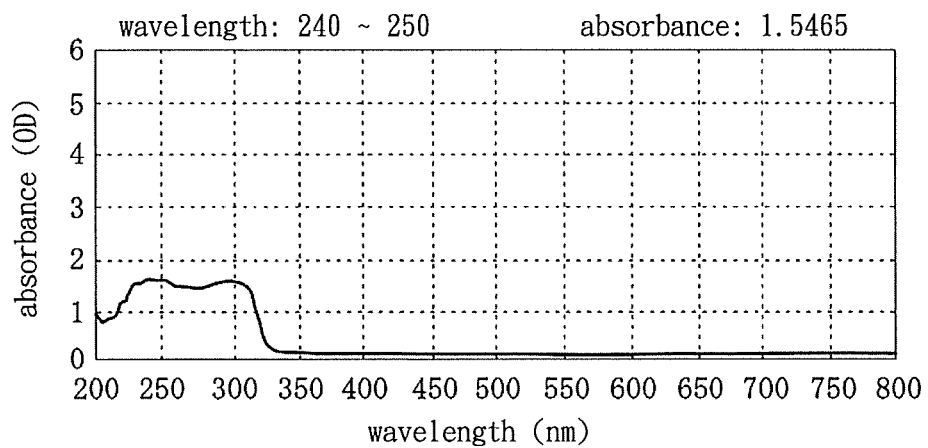
FIG. 2A is a spectrogram of a plastic 1 (PET) which is transparent and in gloss finish according to an embodiment of the present invention.
Figure 2B:
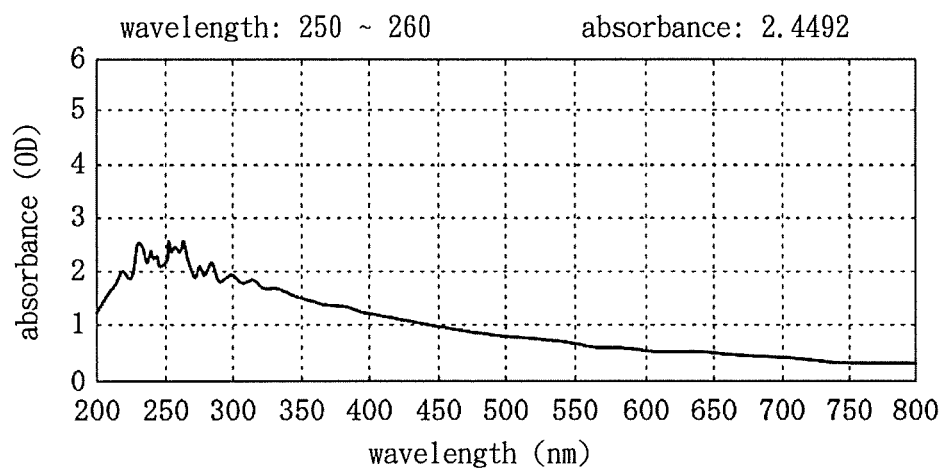
FIG. 2B is a spectrogram of a plastic 2 (HDPE) which is white and in matt finish according to an embodiment of the present invention.

The plastic materials in number 1 to 7 which have similar physical/chemical characteristics are distinguishable in the spectrum of the 200 nm-800 nm wavelength range (ranged from ultraviolet to visible light). FIGS. 2A and 2B are spectrograms of a plastic 1 (PET) which is transparent and in gloss finish and a plastic 2 (HDPE) which is white and in matt finish. In the spectrum of the 200 nm-800 nm wavelength range, an absorbance of the plastic 1 (PET) which is transparent and in gloss finish is greatest when a wavelength is 240-250 nm, and the absorbance is 1.5465; and an absorbance of the plastic 2 (HDPE) which is white and in matt finish is greatest when a wavelength is 205-260 nm, and the absorbance is 2.4492. Other plastic materials may also have greatest absorbances in the same wavelength range.

In this embodiment, the spectrometer 144 is set to define the spectrum with the light signal SL in the 200 nm-800 nm wavelength as a correspondence of the spectrum of the waste container 50. Of course, the spectrometer 144 may be set to produce the light signal SL with the spectrum in other wavelength ranges, and the plastic material to be determined (for example, to determined the plastic materials from number 1 to 3) in the wavelength range are distinguishable, but not limited thereto. The light receiver 142 and the spectrometer 144 of the optical spectrum analyzer 140 are members usually used to produce spectrums. Since an interior structure and respective operations of the light receiver 142 and the spectrometer 144 are known to person skilled in the art, they are not described in detail.

The controller 150 is electrically connected to the optical spectrum analyzer 140 and saves a specific spectrum of each one said plastic material. That is, if the controller 150 is to determine if the waste container 50 is made of the plastic material, for example, the plastic 1 (PET) which is transparent and in gloss finish or the plastic 2 (HDPE) which is white and in matt finish, the controller 150 has to save the specific spectrums of the plastic 1 (PET) which is transparent and in gloss finish and the plastic 2 (HDPE) which is white and in matt finish. In this embodiment, the specific spectrum of each said plastic material can be represented with first few greatest absorbances in the spectrum, and the controller 150 saves the first few greatest absorbances of the each said plastic material.

Then, the controller 150 determines if the spectrum of the waste container 50 is one of the specific spectrums. Specifically, the controller 150 receives the spectrum with the light signal SL in 200 nm-800 nm wavelength range and retrieve the greatest absorbance corresponded so as to determine the greatest absorbance of the spectrum of the waste container 50 is one of the greatest absorbances of the plurality of plastic materials.

If the controller 150 determines the spectrum of the waste container 50 is one of the specific spectrums; that is, if a parameter of the greatest absorbance of the spectrum of the waste container 50 is the same as/similar to a parameter of the greatest absorbance of one said plastic material, the waste container 50 is made of one said plastic material. Then, the controller 150 controls the operation member 110 to conduct a process of recycling the waste container 50. If the controller 150 determines the spectrum of the waste container 50 is not one of the specific spectrums; that is, if a parameter of the greatest absorbance of the spectrum of the waste container 50 is not the same as/similar to a parameter of the greatest absorbance of one said plastic material, the waste container 50 is not made of one said plastic material. Then, the controller 150 controls the operation member 110 to conduct a process of non-recycling the waste container 50.

Accordingly, the waste plastic container recycling system 100 take advantage of the different spectrum characteristics of the plurality of plastic materials which have similar physical/chemical characteristics to determine if the spectrum of the waste container to be recycled is one of the spectrums of the plurality of plastic materials.

In addition, the waste plastic container recycling system 100 further includes an image identification device 160 electrically connected to the controller 150, and the image identification device 160 is neighboring to the waste container 50 and arranged outside of the receiving space 52 of the waste container 50. The image identification device 160 is for identifying if a configuration of the waste container 50 is a specific configuration which represents the plastic material. Preferably, the image identification device 160 identifies the waste container 50 before the determination if the spectrum of the waste container 50 is one of the plurality of specific spectrums. For example, the image identification device 160 is built, in a database with a plurality of configurations of objects to be recycled in advance, such as configurations of iron cans or aluminum cans, plastic or PET bottles, paper boxes, glasses and others, and the configuration of the waste container 50 is a configuration of a common aluminum can.

Therefore, when a user fixedly arranges the waste container 50 around the extension portion 115, the image identification device 160 identifies the configuration of the waste container 50 does not have the specific configuration to represent the plastic material, and the controller 150 controls the operation member 110 to conduct the process of non-recycling the waste container 50. On the contrary, if the configuration of the waste container 50 is the configuration of a common plastic or PET bottle, when a user fixedly arranges the waste container 50 around the extension portion 115, the image identification device 160 identifies the configuration of the waste container 50 has the specific configuration to represent the plastic material, and the controller 150 controls the light generator 130, the optical spectrum analyzer 140 and the operation member 110 to conduct the above-mentioned process of determining if the spectrum of the waste container 50 is one of the specific spectrums of the plastic materials. Therefore, the image identification device 160 can identify images of the configurations of the objects to be recycled to filter objects which are not to be recycled so as to help the waste plastic container recycling system 100 determine if the waste container 50 is made of one of the plurality of plastic materials.

Figure 3:
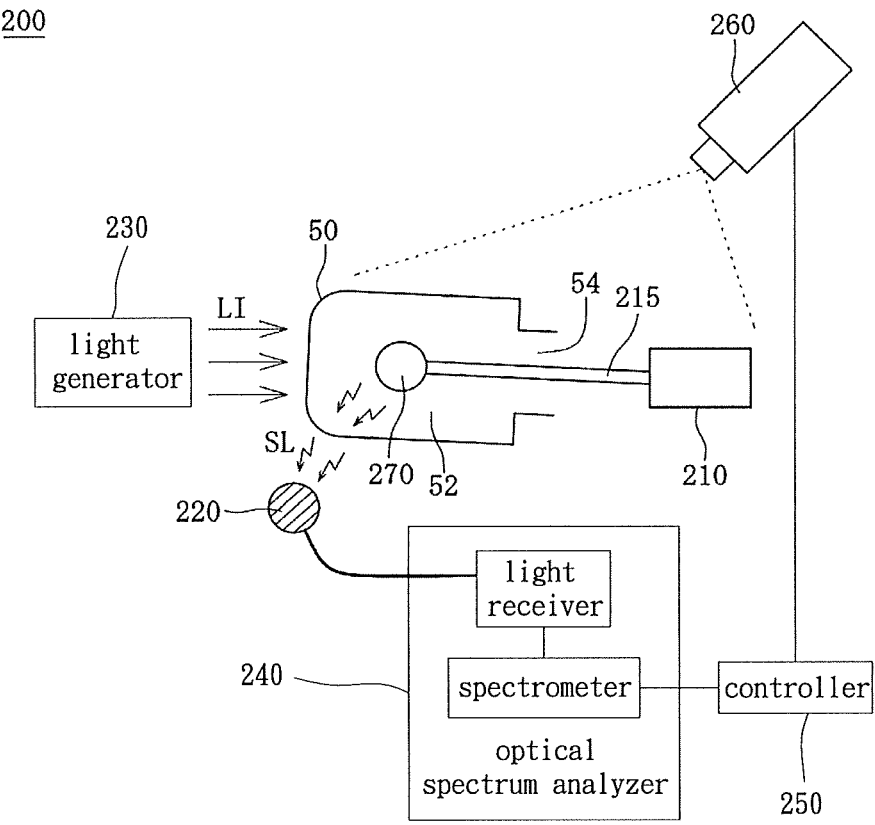
FIG. 3 is a drawing showing another embodiment of the waste plastic container recycling system of the present invention.

Please further refer to FIG. 3 for another embodiment of the waste plastic container recycling system of the present invention. The waste plastic container recycling system 200 includes an operation member 210, a sensing probe 220, a light generator 230, an optical spectrum analyzer 240, a controller 250, an image identification device 260 and a reflecting member 270. Compared with the sensing probe 120 of the previous embodiment which receives the light signal SL which is produced by the light LI entering the waste container 50, the waste plastic container recycling system 200 has the reflecting member 270. The reflecting member 270 is connected to the extension portion 215 for reflecting the light LI entering the waste container 50. The sensing probe 220 is arranged outside the receiving space 52 and electrically connected to a light receiver 242 of the optical spectrum analyzer 240 to receive the light signal SL which is reflected by the light LI entering the waste container 50. That is, when the light generator 230 emits the light LI, and the light LI enters the waste container 50 to configuration the light signal SL which represents the light reflected. The sensing probe 220 receives the light signal SL, and the light signal SL is transmitted through the light receiver 242 to a spectrometer 244 of the optical spectrum analyzer 240 so as to produce the spectrum in a wavelength range needed (for example, the wavelength range between 200 nm to 800 nm).

It is to be noted that if the waste container 50 is an opaque container, most of the light LI is directly reflected by an exterior surface of the waste container 50, and the sensing probe 220 receives the light signal reflected by the waste container and transmits the light signal to the spectrometer 244 of the optical spectrum analyzer 240 to produce the spectrum in the wavelength range needed. If the waste container 50 is a transparent container, most of the light LI enters the waste container 50 and is reflected by the reflecting member 270 to from the light signal SL representing the light reflected (as mentioned in the embodiments above), and the sensing probe 220 receives the light signal SL and transmits the light signal SL to the spectrometer 244 of the optical spectrum analyzer 240 to produce the spectrum in the wavelength range needed.

In addition, the recycling member 270 may be removed from the waste plastic container recycling system 200, and the waste plastic container recycling system 200 may receive the light signal SL which is reflected by the light LI entering the waste container 50 only via the sensing probe 220 arranged outside the receiving space.

The controller 250 which is electrically connected to the spectrometer 244 determines if the spectrum of the waste container 50 is one of the specific spectrums of the plastic materials, and when the controller 250 determines the spectrum of the waste container 50 is one of the specific spectrums of the plastic materials, the controller 250 controls the operation member 210 to conduct the process of recycling the waste container 50.

Therefore, no matter the sensing probe 110 is arranged inside the receiving space 52 of the waste container 50 (which means that the sensing probe 110 receives the light signal SL which is produced by the light LI entering the waste container 50) or outside the receiving space 52 of the waste container 50 (which means that the sensing probe 110 receives the light signal SL which is reflected by the waste container 50), and the optical spectrum analyzer 240 can produce the spectrum in the wavelength range needed based on the signal SL representing the waste container 50.

Figure 4:
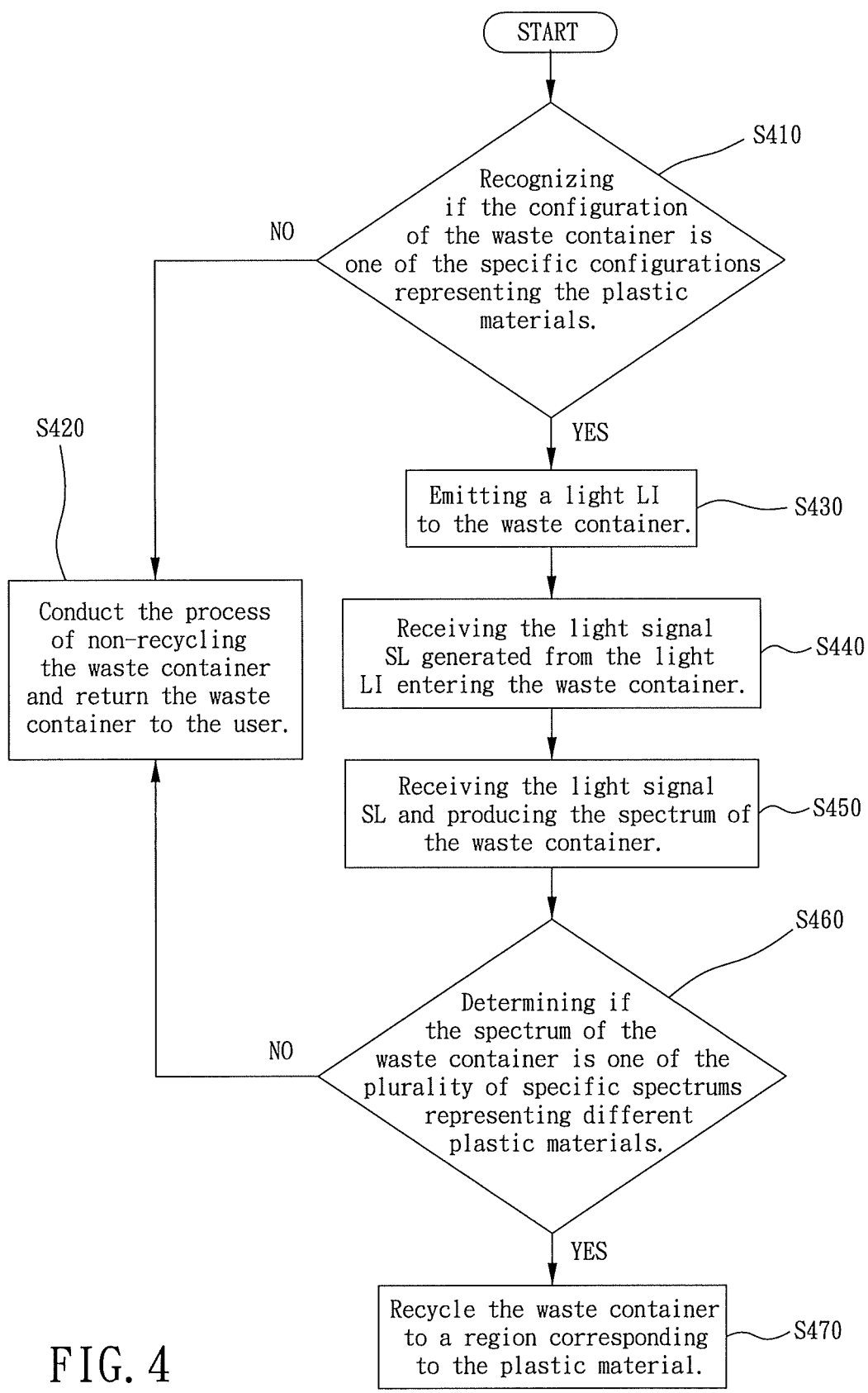
FIG. 4 is a flow chart showing another embodiment of a method for recycling a waste plastic container of the present invention.

In addition, a method for recycling a waste plastic container which is adapted to the waste plastic container recycling system is provided. Please refer to FIG. 4 as well as FIGS. 1, 2A and 2B. For illustration, the extension portion of the operation member is inserted in the receiving space 52 of the waste container 50 for the waste plastic container recycling system 100 to determine if the waste container 50 is one of the plurality of plastic materials and recycle the waste container based on the plastic material thereof.

First, the image identification device 160 of the waste plastic container recycling system 100 identifies if the configuration of the waste container 50 is one of the specific configurations representing the plastic materials (step S410). If the image identification device 160 identifies that the configuration of the waste container 50 is not one of the specific configurations representing the plastic materials, the waste container 50 may be an iron can or an aluminum can, a paper box or other specific configurations which are not plastic or PET bottles. At this moment, the controller 150 of the waste plastic container recycling system 100 controls the operation member 110 to conduct the process of non-recycling the waste container 50 (for example, returning the waste container 50 to the user) (step S420).

On the contrary, if the image identification device 160 identifies the configuration of the waste container 50 is the specific configuration representing the plastic material, the waste plastic container recycling system 100 will further determine the plastic material of the waste container 50. At this moment, the light generator 130 of the waste plastic container recycling system 100 emits a light LI to the waste container 50 (step S430). Then, the sensing probe 120 of the waste plastic container recycling system 100 receives the light signal SL which is produced by the light LI entering the waste container 50, and the light signal SL represents the reflecting light which is formed by the light LI entering the waste container 50 (step S440). The sensing probe 120 is connected to the extension portion 115, and preferably on a top portion 115a of the extension portion 115 so as to receive the light signal SL more preferably. In other embodiments, the sensing probe 120 of the waste plastic container recycling system 100 receives the light signal SL which is produced by the light LI entering the waste container 50. The waste plastic container recycling system 100 has a reflecting member (like the reflecting member 270 in FIG. 3), the reflecting member is connected to the extension portion 115 for reflecting the light signal SL which is produced by the light LI entering the waste container 50, and the sensing probe 120 is arranged outside the receiving space 52 (like the sensing probe 220 in FIG. 3) to receive the light signal SL which is produced by the light LI entering the waste container 50 and which represents the reflecting light.

The optical spectrum analyzer 140 of the waste plastic container recycling system 100 receives the light signal SL and produces the spectrum of the waste container 50 (step S450), and the controller 150 of the waste plastic container recycling system 100 determines if the spectrum of the waste container 50 is one of the plurality of specific spectrums representing different plastic materials (step S460). If the controller 150 determines the spectrum of the waste container 50 is (the same or similar to) one of the plurality of specific spectrums, it means that the waste container 50 is made of a plastic material which is recyclable, and the controller 150 will control the operation member 110 to conduct the process of recycling the waste container 50 and recycle the waste container 50 to a region corresponding to the plastic material (step S470). On the contrary, if the controller 150 determines the spectrum of the waste container 50 is not one of the plurality of specific spectrums, it means that the waste container 50 is made of a plastic material which is unrecyclable, and the controller 150 will control the operation member 110 to conduct the process of non-recycling the waste container 50 and return the waste container 50 to the user (step S420).

Given the above, the waste plastic container recycling system and the method thereof is provided for determining if the spectrum of the container to be recycled is one of the spectrums of the spectrums of the plurality of plastic materials and categorizing the waste containers made of different plastic materials since the plurality of plastic materials which have similar physical/chemical characteristics have different spectrums. In addition, the waste container tilts toward the ground and is arranged around the extension portion of the operation member of the waste plastic container recycling system so as to exclude the liquid residue in the waste container, and the cleaning nozzle is provided for cleaning the interior surface of the waste container through air-jetting (water-jetting) so that the waste plastic container recycling system can obtain the spectrum of the waste container more precisely. The waste plastic container recycling system and the method thereof can recognize the waste plastic containers made of different plastic materials precisely regardless of the appearance, or damage, deformation or concealment of the label on the waste containers.

While we have shown and described various embodiments in accordance with the present invention, it should be clear to those skilled in the art that further embodiments may be made without departing from the scope of the present invention.

What is claimed is:

1. A waste plastic container recycling system, for determining if a waste container is made of one of a plurality of plastic materials so as to recycle the waste container accordingly, including:
   a light generator, arranged in a vicinity of the waste container for emitting light to the waste container;
   a sensing probe, arranged in the vicinity of the waste container and corresponding to the light generator to receive a light signal which is produced from the light entering the waste container or from the light being reflected by the waste container;
   an optical spectrum analyzer, electrically connected to the sensing probe for receiving the light signal, producing a spectrum of the waste container based on the light signal;
   a controller, electrically connected to the optical spectrum analyzer, having specific spectrums of respective ones of the plastic materials saved therein, determining if the spectrum of the waste container is identical to any one of the specific spectrums, wherein if the controller determines the spectrum of the waste container is identical to any one of the specific spectrums, a process of recycling the waste container is conducted;
   an operation member; and
   an image identification device, electrically connected to the controller, the image identification device being neighboring to the waste container and arranged outside of a receiving space of the waste container, the image identification device for identifying if a configuration of the waste container is identical to a specific configuration which represents the plastic material, wherein if the image identification device identifies the configuration of the waste container is non-identical to the specific configuration of the plastic material, the controller controls the operation member not to conduct a process of recycling the waste container.

2. The waste plastic container recycling system of claim 1, further including a reflecting member, wherein the operation member has an extension portion, the extension portion is inserted in the receiving space of the waste container, and the reflecting member is assembled on the extension portion for reflecting the light signal which is produced from the light entering the waste container.

3. The waste plastic container recycling system of claim 1, wherein the sensing probe is arranged outside of the receiving space of the waste container.

4. The waste plastic container recycling system of claim 1, wherein the waste container has an opening, the opening communicates with the receiving space, and an acute angle is included between the opening and a ground.

5. The waste plastic container recycling system of claim 4, wherein the operation member has an extension portion, the extension portion is inserted in the receiving space of the waste container, and the sensing probe is connected to the extension portion.

6. The waste plastic container recycling system of claim 5, wherein the extension portion is provided with a cleaning nozzle for cleaning an interior surface of the waste container.

* * * * *